(12) United States Patent
Brocklebank et al.

(10) Patent No.: US 7,809,539 B2
(45) Date of Patent: Oct. 5, 2010

(54) METHOD FOR SELECTING NODE VARIABLES IN A BINARY DECISION TREE STRUCTURE

(75) Inventors: John C. Brocklebank, Raleigh, NC (US); Bruce S. Weir, Seattle, WA (US); Wendy Czika, Cary, NC (US)

(73) Assignee: SAS Institute Inc., Cary, NC (US)

( * ) Notice: Subject to any disclaimer, the term of this patent is extended or adjusted under 35 U.S.C. 154(b) by 360 days.

(21) Appl. No.: 10/313,569

(22) Filed: Dec. 6, 2002

(65) Prior Publication Data

US 2003/0078936 A1 Apr. 24, 2003

Related U.S. Application Data

(62) Division of application No. 09/545,958, filed on Apr. 10, 2000, now Pat. No. 6,532,467.

(51) Int. Cl.
*G06G 7/48* (2006.01)
*G06F 19/00* (2006.01)
*C12Q 1/00* (2006.01)

(52) U.S. Cl. .................. 703/11; 702/20; 435/4
(58) Field of Classification Search ............ 702/19, 702/20, 27; 703/11; 435/4, 6
See application file for complete search history.

(56) References Cited

U.S. PATENT DOCUMENTS

| | | | |
|---|---|---|---|
| 5,335,291 A | 8/1994 | Kramer et al. | |
| 5,335,346 A | 8/1994 | Fabbio | |
| 5,519,319 A | 5/1996 | Smith et al. | |
| 5,650,722 A | 7/1997 | Smith et al. | |
| 5,675,253 A | 10/1997 | Smith et al. | |
| 5,701,395 A | 12/1997 | Stuckman et al. | |
| 5,748,508 A | 5/1998 | Baleanu | |
| 5,761,442 A | 6/1998 | Barr et al. | |
| 5,941,947 A | 8/1999 | Brown et al. | |
| 6,026,397 A | 2/2000 | Sheppard | |
| 6,182,070 B1 | 1/2001 | Megiddo et al. | |
| 6,189,005 B1 | 2/2001 | Chakrabarti et al. | |
| 6,192,360 B1 | 2/2001 | Dumais et al. | |
| 6,263,334 B1 * | 7/2001 | Fayyad et al. ............ | 707/6 |
| 6,286,005 B1 | 9/2001 | Cannon | |
| 6,292,798 B1 | 9/2001 | Dockter et al. | |
| 6,374,292 B1 | 4/2002 | Srivastava et al. | |
| 6,453,206 B1 | 9/2002 | Soraghan et al. | |
| 6,470,079 B1 | 10/2002 | Benson | |
| 6,530,081 B1 | 3/2003 | Hayes, Jr. | |
| 6,532,467 B1 | 3/2003 | Brocklebank et al. | |
| 6,549,861 B1 | 4/2003 | Mark et al. | |
| 6,594,676 B1 | 7/2003 | Moore | |
| 6,601,049 B1 | 7/2003 | Cooper | |
| 6,611,726 B1 | 8/2003 | Crosswhite | |
| 6,625,569 B2 | 9/2003 | James et al. | |
| 6,631,212 B1 | 10/2003 | Luo et al. | |
| 6,650,779 B2 | 11/2003 | Vachtesvanos et al. | |
| 6,675,145 B1 | 1/2004 | Yehia et al. | |
| 6,678,640 B2 | 1/2004 | Ishida et al. | |
| 6,928,398 B1 | 8/2005 | Fang et al. | |
| 6,941,289 B2 | 9/2005 | Goodnight et al. | |
| 6,954,745 B2 | 10/2005 | Rajan | |
| 6,985,779 B2 | 1/2006 | Hsiung et al. | |
| 7,010,495 B1 | 3/2006 | Samra et al. | |
| 7,127,466 B2 | 10/2006 | Brocklebank et al. | |
| 7,136,871 B2 | 11/2006 | Ozer et al. | |
| 7,162,461 B2 | 1/2007 | Goodnight et al. | |
| 7,171,340 B2 | 1/2007 | Brocklebank | |
| 7,171,411 B1 | 1/2007 | Lewis et al. | |
| 7,254,547 B1 | 8/2007 | Beck et al. | |
| 7,340,440 B2 | 3/2008 | Goodnight et al. | |
| 7,533,038 B2 | 5/2009 | Blume et al. | |
| 2002/0099952 A1 | 7/2002 | Lambert et al. | |
| 2003/0110246 A1 | 6/2003 | Byrne et al. | |
| 2003/0174178 A1 | 9/2003 | Hodges | |
| 2004/0073475 A1 | 4/2004 | Tupper | |
| 2004/0148409 A1 | 7/2004 | Davis et al. | |
| 2004/0230829 A1 | 11/2004 | Dogan et al. | |
| 2004/0254934 A1 | 12/2004 | Ho et al. | |
| 2005/0154885 A1 | 7/2005 | Viscomi et al. | |
| 2007/0240106 A1 | 10/2007 | Manson et al. | |

FOREIGN PATENT DOCUMENTS

WO 0157706 8/2001

OTHER PUBLICATIONS

Robbins "Information Infrastructure" IEEE Engineering in Medicine and Biology (1995), pp. 746-759.*
Robbins "Representing Genomic Maps in a Relational Database" Computational Methods in Genome Research (1994), pp. 85-96.*
Bingley et al. "Perspectives in Diabetes: Can We Really Predict IDDM" Diabetes, (1993), vol. 42, pp. 213-220.*
Janikow, Cezary Z., "Fuzzy Decision Trees: Issues and Methods", IEEE Transaction on Systems, Man, And Cybernetics- Part B: Cybernetics, vol. 28, No. 1, Feb. 1998, pp. 1-14.
Mingers, John, "An Empirical Comparison of Selection Measures for Decision-Tree Induction," Machine Learning 3, pp. 319-342, 1989.
Aaker, David A. et al., "On Using Response Latency to Measure Preference", Journal of Marketing Research, vol. XVII, pp. 237-244 [May 1980].
Bass, Frank M. et al., "Testing Distributed Lag Models of Advertising Effect", Journal of Marketing Research, vol. IX, pp. 298-308 [Aug. 1972].

(Continued)

*Primary Examiner*—Eric S Dejong
(74) *Attorney, Agent, or Firm*—Jones Day

(57) ABSTRACT

A method for selecting node variables in a binary decision tree structure is provided. The binary decision tree is formed by mapping node variables to known outcome variables. The method calculates a statistical measure of the significance of each input variable in an input data set and then selects an appropriate node variable on which to base the structure of the binary decision tree using an averaged statistical measure of the input variable and any co-linear input variables of the data set.

20 Claims, 6 Drawing Sheets

OTHER PUBLICATIONS

Blair, Margaret Henderson, "An Empirical Investigation of Advertising Wearin and Wearout", Journal of Advertising Research, pp. 45-50 [Dec. 1987/ Jan. 1988].

Bradlow, Eric T. et al., "Subscale Distance and Item Clustering Effects in Surveys: A New Metric", Journal of Marketing Research, vol. 38, No. 2, pp. 1-24 [May 2001].

Brause, Rudiger W., "Cascaded Vector Quantization by Non-linear PCA Network Layers", IEEE, 1063-6730/94, pp. 154-160 [1994].

Brockwell, Peter J. et al., "Introduction to Time Series and Forecasting", Spring Science+Business Media, Inc., pp. 112-116 [2002].

Cannon, Hugh M. et al., "Effective Reach and Frequency: Does It Really Make Sense?", Journal of Advertising Research, pp. 19-28 [Mar./Apr. 1994].

Chan, Lipchen Alex et al., "Automatic Target Detection Using Dualband Infrared Imagery", Acoustics, Speech, and Signal PICASSP '00 Proceedings, 2000 IEEE International Conference, vol. 6, pp. 2286-2289 [Jun. 5-9, 2000].

Chatterjee, Chanchal et al., "Self-Organizing Algorithms for Generalized Eigen-Decomposition", IEEE Transactions on Neural Networks, vol. 8, No. 6, pp. 1518-1530 [Nov. 1997].

Chen, Qimei et al., "Attitude toward the Site", Journal of Advertising Research, pp. 27-37 [Sep.-Oct. 1999].

Chen, Yupeng et al., "High Resolution Adaptive Bearing Estimation Using a Complex-Weighted Neural Network", IEEE, pp. II-317-II-320 [1992].

Cheung, Natasha, "Outward bound: Should organisations be tempted by the option of outsourcing their CRM applications?", Information Age, http://www.information-age.com/article/2001/july/outward_bound, 5 pp. [Jul. 13, 2001].

Christensen, Raymond P., "Efficient Use of Food Resources in the United States", Technical Bulletin No. 963, pp. 42-45 [Oct. 1948].

Chung, Chanjin et al., "Determinants of Temporal Variations in Generic Advertising Effectiveness", Agribusiness, vol. 16, No. 2, pp. 197-214 [2000].

Clarke, Darral G., "Econometric Measurement of the Duration of Advertising Effect on Sales", Journal of Marketing Research, vol. XIII, pp. 345-357 [Nov. 1976].

Corkindale et al., "Advertising Thresholds and Wearout", European Journal of Marketing, vol. 12, No. 5, pp. 329-350, 359-373 [1978].

Dawar, Niraj, "Extensions of Broad Brands: The Role of Retrieval in Evaluations of Fit", Journal of Consumer Psychology, vol. 5, No. 2, pp. 189-207 [1996].

Dholakia, Utpal M. et al., "What makes commercial Web pages popular? An empirical investigation of Web page effectiveness", European Journal of Marketing, vol. 32, No. 7/8, pp. 724-736 [1998].

Hu, The-Wei et al., "The State Antismoking Campaign and the Industry Response: The Effects of Advertising on Cigarette Consumption in California", The American Economic Review, vol. 85, No. 2, Papers and Proceedings of the Hundredth and Seventh Annual Meeting of the American Economic Association Washington, DC Jan. 6-8, 1995, pp. 85-90 [May 1995].

Krishnamurthi, Lakshman et al., "Intervention Analysis of a Field Experiment to Assess the Buildup Effect of Advertising", Journal of Marketing Research, vol. XXIII, pp. 337-345 [Nov. 1986].

Lee, Jonq-Ying et al., "Lag Structures in Commodity Advertising Research", Agribusiness, vol. 8, No. 2, pp. 143-154 [1992].

Liu, Donald J. et al., "Generic Fluid Milk Advertising, Demand Expansion, and Supply Response: The Case of New York City", Amer. J. Agr. Econ., pp. 229-236 [May 1988].

Mehrotra, Kishan et al., "Elements of Artificial Neural Networks", MIT, pp. 11, 25, 71, 76, 85-87, 157, 170 and 171 [1997].

Pham, Michel Tuan et al., "Analyzing the Memory Impact of Advertising Fragments", Marketing Letters, vol. 8, No. 4, pp. 407-417 [1997].

Pritchett, James G. et al., "Optimal Choice of Generic Milk Advertising Expenditures by Media Outlet", Journal of Agricultural and Resource Economics, vol. 23, No. 1, pp. 155-169 [1998].

Simon, Julian L. et al., "The Shape of The Advertising Response Function", Journal of Advertising Research, Vo. 20, No. 4, pp. 11-28 [Aug. 1980].

Tellis, Gerard J. et al., "Does TV Advertising Really Affect Sales? The Role of Measures, Models, and Data Aggregation", Journal of Advertising, vol. 24, No. 3, pp. 1-12 [Fall 1995].

Vakratsas, Demetrios et al., "How Advertising Works: What Do We Really Know?", Journal of Marketing, vol. 63, pp. 26-43 [Jan. 1999].

Venkateswaran, Meenakshi et al., "Modeling Advertising Carryover in Fluid Milk: Comparison of Alternative Lag Specifications", Agricultural and Resource Economics Review, vol. 22, No. 1, pp. 10-19 [Apr. 1993].

Wilkins, Nick et al., "Tool 3. Demand Analysis: Economic Analysis of Tobacco Demand", World Bank Economics of Tobacco Toolkit, pp. 1-100 [2001].

Wong, A.S.Y et al., "A Unified Sequential Method for PCA", IEEE, pp. 583-586 [1999].

SAS/ETS Software, as evidenced by User's Guide to SAS/ETS Software, SAS Institute Inc., http://www.uc.edu/sashtml/ets/index.html, pp. 1-41 [1999].

* cited by examiner

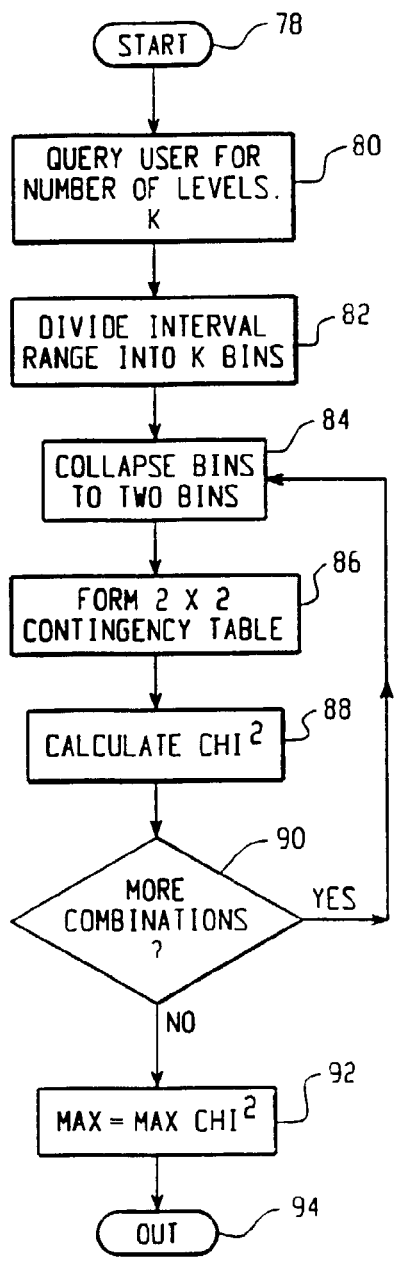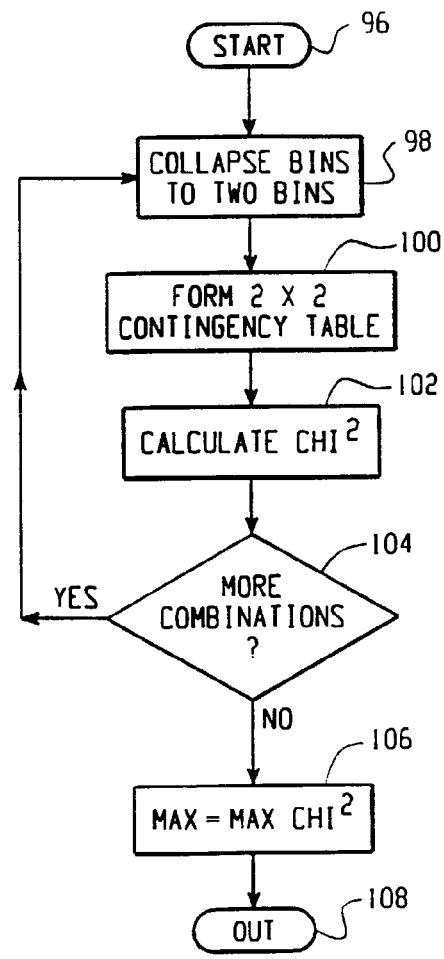
Fig. 3A
(PRIOR ART)
Fig. 3B
(PRIOR ART)

METHOD FOR SELECTING NODE VARIABLES IN A BINARY DECISION TREE STRUCTURE

CROSS-REFERENCE TO RELATED APPLICATION

This application claims priority to and is a divisional of U.S. patent application Ser. No. 09/545,958 filed on Apr. 10, 2000 now U.S. Pat. No. 6,532,467. By this reference, the full disclosure, including the drawings, of said U.S. patent application is incorporated herein.

BACKGROUND OF THE INVENTION

1. Field of the Invention

The present invention is directed toward the field of data mining. More specifically, the invention provides a method of selecting particular variables from a large data set containing a plurality of variables to be used as nodes in a binary decision tree. The invention is particularly useful with large data sets in which some variables are partly co-linear. An example of this type of large data set is genomic data taken from human chromosomes which can be used to associate genotypic data with disease status.

2. Description of the Related Art

Binary decision trees are known in the field of data mining. Generally, the decision tree utilizes a search method to choose the best variable on which to base a particular decision making process. The best variable is chosen from a set of input variables in an input data set, where the outcome measure is known for each set of input variables. A hierarchy of decisions are built into the decision tree using a "yes/no" structure in order to arrive at an outcome from a set of known possible outcomes. At each node of the decision tree, the input data set is split into two subsets based on the value of the best variable at that point in the binary tree structure. The best variable is thus defined as the "node variable" because it is the variable that the decision tree branches from at that point in the path of the decision making process. The tree continues to branch to the next best available variable until some minimum statistical threshold is met, or until some maximum number of branches are formed. A subsequent set of input data values for each of the variables can then return a predicted outcome.

Using a binary decision tree is particularly useful in the study of genomic mapping. In such a study, a binary tree is constructed to match genetic markers to a phenotypic trait. One such phenotypic trait could be disease status. In this example, the binary tree categorizes whether or not a subject is likely to have a particular disease by selecting a path through the tree based on the values of the specific markers that form the nodes of the tree. The input data set can then be categorized into one of the disease outcomes, either affected or not affected.

A known method for selecting the node variable that forms a node of the tree branch for the example genomic application is shown in FIG. 1. An input data set 10 includes a plurality of rows 12, each row defining a subject. Each column 14 describes a particular variable. The first variable is typically a patient identifier. Clinical variables 16, such as age and weight, are shown in columns 3 to N+1 where N is the number of clinical variables 16. Clinical variables 16 are variables that can generally be taken by an examiner or through a set of simple questions asked of the patient. In the columns after the clinical variables 16, a plurality of genomic markers ("marker variables") 18, taken from the DNA of a cell of the patient, are recorded. In this example, twenty-five genetic markers 18 are recorded from each patient. The recording of the markers 18 requires utilizing at least one specialized instrument to take a sample and record the values of each of the twenty-five markers 18. The disease state 20 is the final column in the data set, and it is the outcome measure of the data set 10, i.e. whether the particular patient is affected or not. The disease state 20 is known for each subject in the input data set 10.

For each variable (clinical and marker), the values are binned into two groups. For instance, the clinical variable "sex" is binned into a male group and a female group. Other variables, such as the clinical variable "age" are considered interval variables. An interval variable is a variable that has a continuous distribution over a particular range. The interval variable is initially separated into a user-defined number of bins. These bins are then grouped to form two bins. For example, the clinical variable age might first be reduced to 10 levels of 10 years each. The 10 levels will be grouped into 2 bins, based on the results of a statistical test described below. The process of reducing the variable to two bins will first measure the first level against the second through the tenth levels. The process continues by measuring the first and second levels against the third through the tenth, until eventually the first nine levels are measured against the tenth level. The best statistical result will define the delineation point for the variable.

The marker variables 18 are categorized by a bi-allelic genotype. Generally, these genotypes are referred to as AA, Aa, or aa. AA is the homozygote genotype for allele A, Aa is the heterozygous genotype, and aa is the homozygote genotype for allele a. Since three bi-allelic genotypes exist, the two bins are separated 30 into a pair of two genotypes and a single genotype for each marker 18. This binning is accomplished by a similar statistical step as the binning of the clinical variables. Once the binning is completed, a statistical measure of correlation is calculated for each marker. An example of such a statistical calculation is the chi squared statistic as referenced in "Principles and Procedures of Statistics a Biometrical Approach", pages 502-526, which is incorporated by reference herein. A plot 40 of one set of the chi-squared statistic is shown in FIG. 1. A large chi-squared statistic suggests a marker that is highly associated with the disease state. The most highly associated marker is selected for the first node in the binary tree by selecting the largest chi squared statistic.

More specifically, the steps of building a binary decision tree for analyzing this type of data set is shown in FIGS. 2 and 3. FIG. 2 shows the method of building the decision tree. FIGS. 3A and B show the steps of creating the two bins for each variable. FIG. 3A shows the steps of creating the two bins for an interval variable, and FIG. 3B shows the steps of forming the two bins for variables other than interval variables.

Turning now to FIG. 2, the input data set 10 is provided to the method in step 50. The method is generally implemented as a software program operating on a general purpose computer system. At step 52, the user enters a number of algorithmic parameters, such as the number of passes the user wishes the tree to branch to, a minimum value for the least significant chi square statistic, and the number of inputs. An input counter, "i", and a maximum value, "MAXSOFAR", are initialized at step 52. The first variable is then retrieved from the input data set for all subjects. Step 54 determines if the first variable is an interval variable. If the first variable is an interval variable, then it is passed to step 56 where the steps of FIG. 3A return a TEST value of the best chi square statistic from the two bin structure of the particular variable. If, however, the first variable is not an interval variable, then it is passed to the steps of FIG. 3B in step 58, which also returns a TEST value indicating the best chi square statistic for the particular variable.

Step 60 determines if the TEST value from step 56 or step 58 is greater than the MAXSOFAR value, i.e., is the chi-squared statistic for the current variable larger than the chi-squared values for all the previously analyzed variables. If the TEST value is greater, then the TEST value is stored 62 as the MAXSOFAR value and the input counter is updated 64. If the TEST value is not larger than MAXSOFAR, then the input counter is updated 64 without storing the TEST result. Step 66 determines if the input counter (i) is less than the number of input variables in the data set. If the input counter (i) is less than the number of inputs, control returns to step 54 using the next variable for the determining step 54. Once the input counter (i) is equal to the number of input variables, step 68 determines if MAXSOFAR is less than a user-defined parameter, MINCHISQ, which is the minimum significant chi-squared statistic the user wants to retain in the binary tree. If maxsofar is less than MINCHISQ, the binary tree is output in step 70. If MAXSOFAR is greater than MINCHISQ, then step 72 determines if the number of passes is less than the maximum number of passes the user has set. If the number of passes is greater than the maximum number of passes, then the variables chosen as node variables are passed to the output step 70. If, however, the maximum number of passes has not been reached, then at step 76 the data set is divided into two data sets based on the two bins that were used to determine the best chi square statistic and control reverts back to step 52, where the counter variables are reset and another pass through the algorithm is executed.

FIG. 3A generates the chi-squared statistic for interval variables. Step 78 starts the process. Step 80 queries the user for the number of levels the variable will be split into, and defines it as k. The interval range (maximum value of the variable minus the minimum value of the variable) is divided 82 into k bins. The k bins are then collapsed in step 84 into two bins. A 2×2 contingency table is formed in step 86 and then the chi squared statistic is calculated at step 88. Step 90 determines if more combinations of splitting the k bins into 2 bins can be accomplished. If another combination that has not been tested exists, the process returns to step 84. If no more combinations exists, step 92 finds the maximum value of the chi-squared statistic from the combinations tested, and returns this value as the TEST value in step 94.

FIG. 3B generates the chi-squared statistic for non-interval variables. Step 96 starts the process. The variable is collapsed 98 into two bins. The 2×2 contingency table is formed 100 and then the chi squared statistic is calculated 102. Step 104 determines if more combinations of splitting the variable into 2 bins can be accomplished. If another combination that has not been tested exists, the process returns to step 98. If no more combinations exists, step 106 finds the maximum value of the chi-squared statistic from the combinations, and returns this value as the TEST value in step 108. For example, a marker variable has three possible genotypes, AA, Aa or aa. These variables can be combined into three different bin combinations (AA and Aa, Aa and aa, AA and aa).

Using this process (FIG. 2) for genomic data, if the largest chi-squared statistic was generated, for example, at marker 18, the data set would be split into two subsets based on the value of marker 18. As shown in FIG. 4, the two data sets would be split as Data Set 1 and Data Set 2. Data Set 1 includes patients whose value for marker 18 is the bi-allelic genotype AA or Aa. Data Set 2 includes patients whose bi-allelic genotype is aa. Each data set would then be passed back to step 52 where the process of determining the best bins for each variable, calculating the chi-squared statistic for each remaining variable, and then recording the variable with the largest chi-squared statistic (the node variable) would be repeated. This process of determining the node variables at each pass through the algorithm is repeated until one of the parameter thresholds is met (either MINCHISQ or the maximum number of passes). Each pass through the algorithm builds another layer into the decision tree.

Genomic data, such as the marker genotypes, can be correlated with nearby neighbors. One problem of the prior art method is that it is possible for a false identifier to have a large chi-squared statistic in such a large data set. A false identifier will branch a binary tree at a marker location that is not a good predictor of the disease state. Further branching of the tree after a false identifier could produce minimal results. An example of a false identifier 120 is shown in the plot 40 of FIG. 1. The peak of the false identifier 120 is the largest peak in the chi-squared data, but the peak does not represent the best choice for the node variable because the secondary peak 122 shows a more pronounced region of large chi-squared values. Since it is known that adjacent neighbors are correlated, the secondary peak 122 is a better choice for the node variable. The prior art method can not identify a false positive identifier and therefore would use the false identifier as the node variable at that level of the decision tree.

SUMMARY OF THE INVENTION

A method for selecting node variables in a binary decision tree structure is provided. The binary decision tree is formed by mapping node variables to known outcome variables. The method calculates a statistical measure of the significance of each input variable in an input data set and then selects an appropriate node variable on which to base the structure of the binary decision tree using an averaged statistical measure of the input variable and any co-linear input variables of the data set.

One aspect of the current invention provides a method of selecting node variables for use in building a binary decision tree. The method comprises the step of providing an input data set which includes a plurality of input variables and an associated decision state. A statistical measure of the significance of each of the input variables to the associated decision state is calculated. The statistical measure is averaged for each input variable and nearby variables. The largest statistical measure is chosen and the variable associated with the largest statistical measure is used as a node variable for splitting the input data set into two subsets.

Another aspect of the current invention provides a method for mapping genomic markers to a phenotypic trait. The method comprises the steps of receiving a structured data set having a plurality of genomic markers. A first correlating statistic is determined for each genomic marker proportional to the capability of the genomic marker to map the phenotype. A second correlating statistic is calculated using the value of the first correlating coefficient and values of nearby first correlating statistics. The largest second correlating statistic is selected and the variable associated with the largest second correlating statistic is used as a decision node of a binary decision tree.

BRIEF DESCRIPTION OF THE DRAWINGS

FIG. 3A is a flow chart more specifically showing one of the steps of the prior art data mining method of FIG. 2;

FIG. 3B is a flow chart also showing one of the steps of the prior art data mining method of FIG. 2;

DETAILED DESCRIPTION OF THE DRAWINGS

Figure 5A:
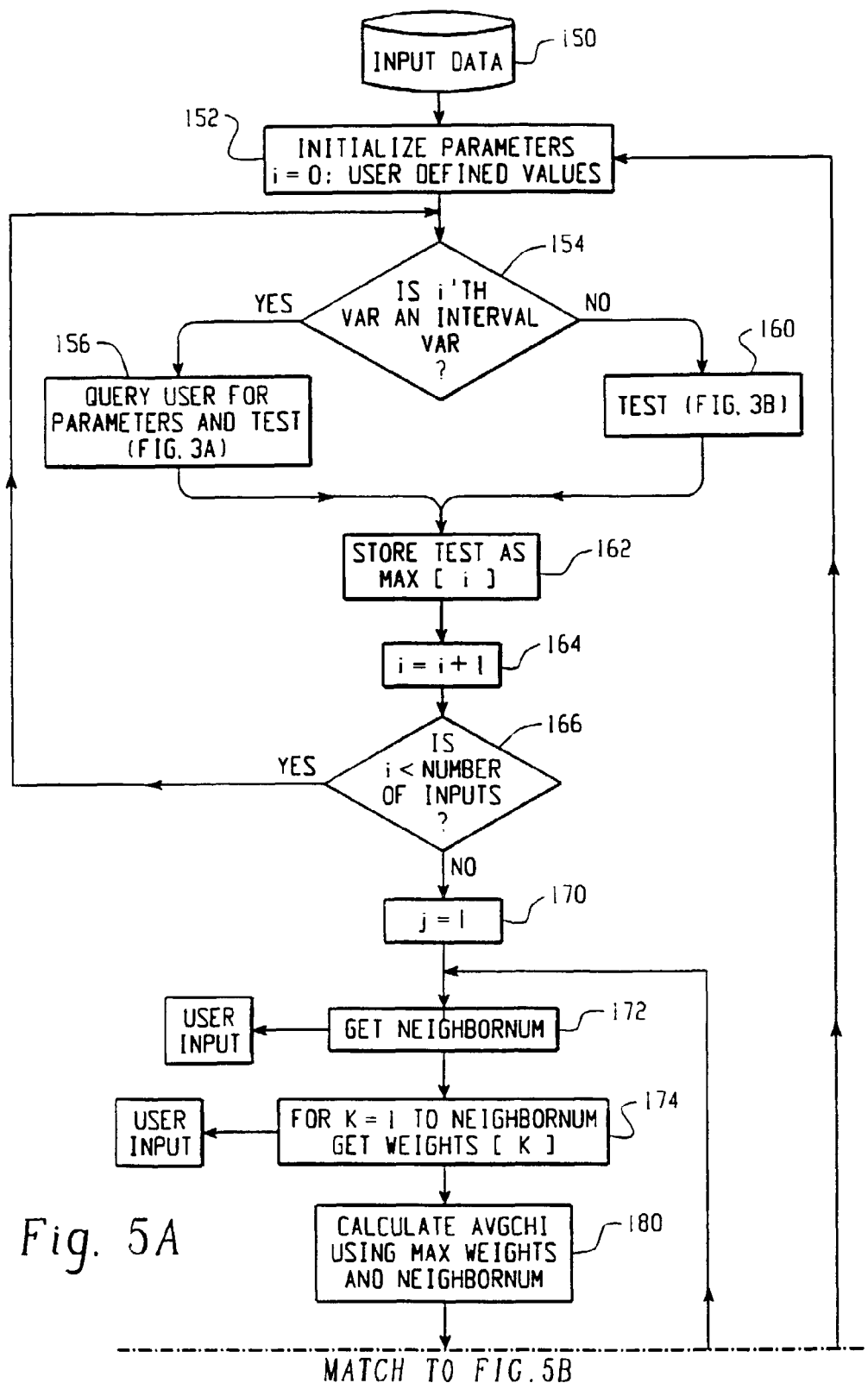
FIG. 5 is a flow chart of a preferred embodiment of the data mining method of the present invention.
Figure 5B:
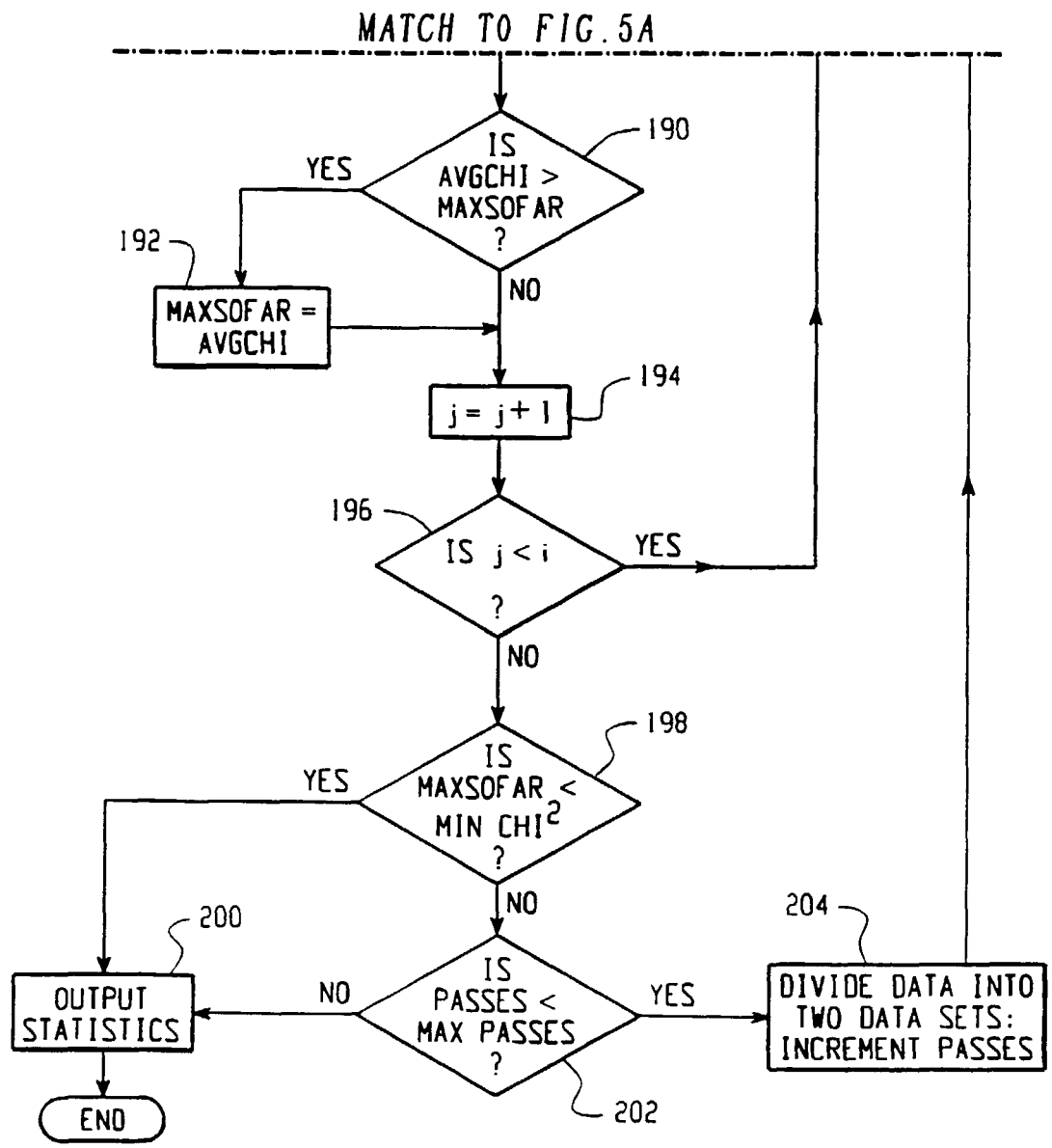

FIG. 5 sets forth a flow chart of the preferred method steps for selecting node variables in a binary decision tree according to the present invention. Preferably, the method steps are embodied in a software program. The software program can be recorded on a memory device such as a magnetic disk, or CD-ROM, or located on a host system accessible to client machines. The software program could be distributed between a number of host computers so that the computers may process the steps of the method in parallel. Likewise, the data mining method could be implemented in a hardware configuration or other configurations.

The method begins at step 150, where the input data set is retrieved. At step 152 various algorithmic parameters are initialized, and the user may be queried to input values for other parameters ("user-defined parameters"), such as a value for the number of passes the method will execute on the input data set. This gives the user the ability to set the maximum number of nodes for a decision tree (i.e., the depth of the decision tree).

Another user-defined parameter may be a minimum chi-squared parameter, MINCHISQ. This parameter is used to determine when the calculated value of the maximum chi-squared statistic for the best variable is no longer relevant to the decision making process. The chi-squared statistic is a measure of the difference between the value of the variable and the expected value of the variable. A large chi-squared value, thus, shows a large difference between the expected value and the true value. If all variables are assumed to predict the outcome equally well, a large chi-squared value is associated with a variable that is a very good predictor of the outcome, and is thus a desired variable to choose as a decision making node in building a binary decision tree. The MINCHISQ parameter allows the user to define the least significant chi squared value that can be used to select a node variable.

At step 154, the software determines whether the current variable, the "i'th" variable, is an interval variable. If the current variable is an interval variable, then step 156 executes the steps shown in FIG. 3A and returns a TEST value for the chi-squared statistic and the proper binned combination for the current variable. If, however, the variable is not an interval variable, then at step 160 the steps shown in FIG. 3B are executed, which returns a TEST value for the chi-squared statistic. Control then passes to step 162 where the value of TEST is stored into an array MAX[i] at the i'th position determined by the current value of the input counter (i). The value of the input counter (i) is incremented in step 164 and step 166 determines if input counter (i) is less than the number of input variables in the input set. If input counter (i) is less than the number of inputs, the method returns to step 154 using the incremented value of input counter (i) to test the next input variable.

If the input counter (i) is not less than the number of inputs, then step 170 sets the temporary counter j to 1. Step 172 then queries the user for the number of adjacent variables on both sides of the j'th current variable, NEIGHBORNUM, that the user would like to include in determining the weighted average for the j'th current variable. When the user has set the number of neighbors, step 174 then queries the user 2*NEIGHBORNUM+1 times for a weight to associate with each neighbor variable value. The results of the query are stored in a WEIGHTS array. When the parameters are set for the current j'th variable, step 180 calculates an average chi-squared value, AVGCHI. The value AVGCHI is calculated using the stored values in the MAX array, the WEIGHTS array, and the NEIGHBORNUM value, as follows.

$$AVGCHI(j) = \frac{\sum_{k=-NEIGHBORNUM}^{NEIGHBORNUM} WEIGHTS[k+NEIGHBORNUM]*MAX[j+k]}{\sum_{k=0}^{2*NEIGHBORNUM} WEIGHTS[k]}. \quad [1]$$

Step 190 determines whether the AVGCHI value calculated for the j'th variable is greater than the current MAXSOFAR value. If AVGCHI is greater than MAXSOFAR, then MAXSOFAR is set to the current value of AVGCHI in step 192. If the AVGCHI value is not greater than MAXSOFAR, then MAXSOFAR is not updated with the new value of AVGCHI. Step 194 updates the temporary counter (j) and step 196 determines if the updated temporary counter (j) is less than the number of variables of the input counter (i). If temporary counter (j) is less than input counter (i), the method returns to step 172 and queries the user for the parameters NEIGHBORNUM and WEIGHTS to calculate the AVGCHI value for the new j'th variable.

If the temporary counter (j) equals the input counter (i), step 198 tests if MAXSOFAR is less than the parameter MINCHISQ. If MAXSOFAR is less than MINCHISQ, then the binary tree has been fully developed, and the node variables are output in step 200 into a binary tree structure for processing of future input data sets. If MAXSOFAR is greater than MINCHISQ, step 202 determines if the number of passes is less than the maximum number of passes. If the number of passes is not less than the maximum number of passes, the node variables are passed to the output step 200. If the number of passes is less than the maximum number of passes, step 204 divides the data set into two data sets based on the bin information from the TEST variable. Step 204 also increments the number of passes that have occurred. Control returns to step 152 where the process begins again with the new partial data sets. When one of the thresholds (MINCHISQ or number of passes) is reached, all of the variables that have been chosen as node variables are output to form the binary decision tree structure. A future input data set then can be directed through the decision tree and a measure of the likelihood a patient is susceptible to having contracted the particular disease may be obtained based upon the decision tree The invention thus minimizes the effect of a single false point where the value of the chi-squared statistic is large. The use of weights for adjacent variables will return a chi-squared statistic that is an average of the local values of the variables. In such a case where a single false positive identifier would normally be the largest chi-squared statistic and thus become a decision based node for the binary tree, the weighted averaging method will instead choose a better variable. The results of using this method are shown in the plot 210 of FIG.

Figure 1:
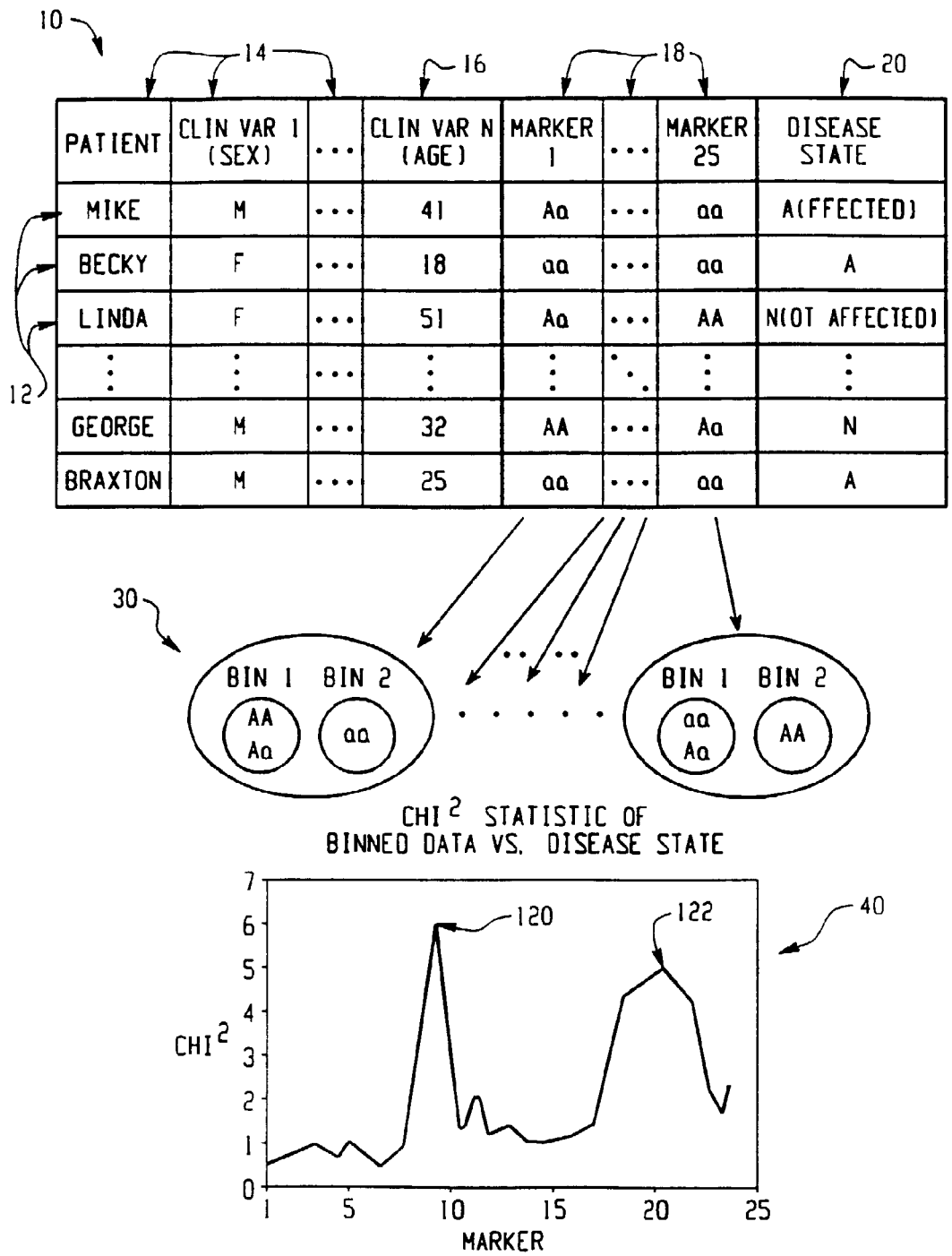
FIG. 1 is a diagram of a prior art data mining method.
Figure 2:
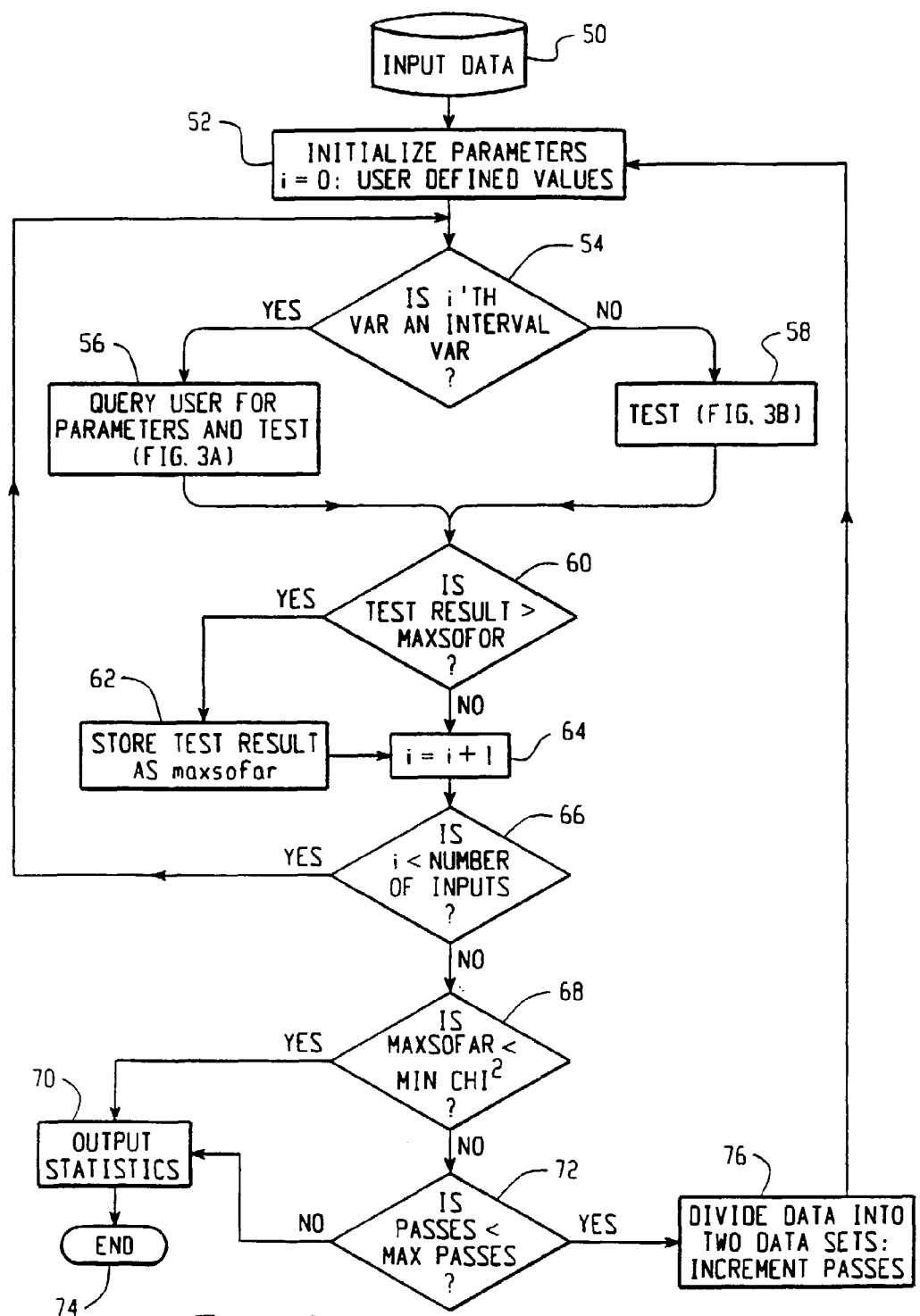
FIG. 2 is a flow chart of the prior art data mining method of FIG. 1.
Figures 4, 6:
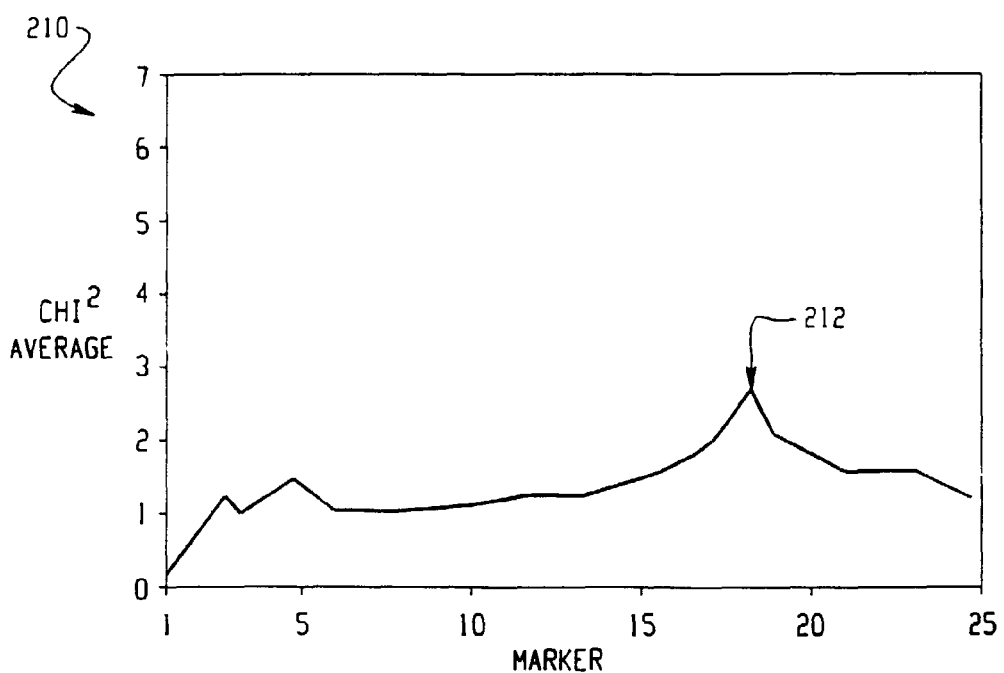
FIG. 4 is a pair of data sets showing the results of a single pass through the prior art data mining method of FIG. 2.
FIG. 6 is a plot of the results of the inventive data mining method for an example data set.

6. The peak 212 of FIG. 6 is the highest point in the plot. Any single point that might have produced a highest peak has been smoothed from the data results.

This method works particularly well with a data set that is ordered in a manner known to the user. The user understands the correlation between nearby input variables, the user can thus assign weights intelligently. For example, in the case of genomic data sets, many clinical variables may be unrelated to nearby clinical variables, and the weights of adjacent variables will be very small, and can be zero. The markers 18 taken from the sample cells are taken along the length of a chromosome. Because it is known that markers 18 along the length of a chromosome are related, this method gives the user a means for using the collinearity of the adjacent markers to make better decisions as to which variable is chosen as a node in the binary tree structure. This method is particularly useful for genomic data because of the known collinearity of the genomic markers, but is also applicable to data sets where it is known that collinearity exists between groups of input variables.

The preferred embodiments described with reference to the attached drawing figures are presented only to demonstrate certain examples of the invention. Other elements, steps, methods and techniques that are insubstantially different from those described above and/or in the appended claims are also intended to be within the scope of the invention.

The invention claimed is:

1. A computer-implemented method for mapping one or more genomic markers to a phenotypical trait, the method comprising:

receiving, using one or more processors, a structured data set having a plurality of genomic markers;

determining, using one or more processors, a first correlating statistic for each genomic marker where the magnitude of the correlating statistic is proportional to the capability of the genomic marker to map a phenotype; and calculating, using one or more processors, a second correlating statistic for each genomic marker from a smoothing mathematical function of the determined first correlating statistic of the genomic marker and the first correlating statistic of adjacent genomic markers, wherein calculating includes:

providing a neighbor parameter indicating how many adjacent genomic markers to use in calculating the second correlating statistic, and providing a weight parameter indicating a weight to apply to each of the adjacent genomic markers used in calculating the second correlating statistic, and calculating the second correlating statistic for each genomic marker according to the following equation:

$$AVGCHI(j) = \frac{\sum_{k=-NEIGHBORNUM}^{NEIGHBORNUM} WEIGHTS[k+NEIGHBORNUM] * MAX[j+k]}{\sum_{k=0}^{2*NEIGHBORNUM} WEIGHTS[k]},$$

wherein NEIGHBORNUM is the neighbor parameter, WEIGHTS is an array of weight parameters having length NEIGHBORNUM, and MAX is the first correlating statistic.

2. The method of claim 1, further comprising:

repeatedly splitting the structured data set a predetermined number of times.

3. The method of claim 1, wherein the first correlating statistic is a chi-squared statistic.

4. The method of claim 1, wherein the phenotypical trait is whether a particular individual set of input genomic markers are associated with a disease.

5. The method of claim 1, wherein a genomic marker in the structured data set has one or more neighbor genomic markers; and wherein calculating the second correlating statistic measure includes averaging the first correlating statistics for a genomic marker and one or more neighbor genomic markers.

6. The method of claim 5, wherein the plurality of genomic markers in the structured data set have an order; wherein the order is used to determine which genomic markers are neighbors of a particular genomic marker; and wherein a change in the order of the genomic markers affects the averaging of the first correlating statistics.

7. The method of claim 1, wherein the plurality of genomic markers in the structured data set are co-linear.

8. The method of claim 5, wherein the averaging of the first correlating statistics results in a smoothing of the structured data set.

9. The method of claim 8, wherein the smoothing of the structured data set includes eliminating one or more false identifiers from the structured data set.

10. The method of claim 1, wherein receiving the structured data set, determining the first correlating statistic, and calculating the second correlating statistic are performed using a data mining software application.

11. The method of claim 1, wherein the plurality of genomic markers are from DNA of a patient.

12. The method of claim 11, further comprising:

categorizing whether the patient is more likely than not to have a disease.

13. A computer-implemented system for mapping genomic markers to a phenotypical trait, comprising:

one or more processors;

one or more computer-readable storage mediums containing software instructions executable on the one or more processors to cause the one or more processors to perform operations including:

receiving a structured data set having a plurality of genomic markers;

determining a first correlating statistic for each genomic marker where the magnitude of the correlating statistic is proportional to the capability of the genomic marker to map a phenotype; and calculating a second correlating statistic for each genomic marker from a smoothing mathematical function of the determined first correlating statistic of the genomic marker and the first correlating statistic of adjacent genomic markers, wherein calculating includes:

providing a neighbor parameter indicating how many adjacent genomic markers to use in calculating the second correlating statistic, and providing a weight parameter indicating a weight to apply to each of the adjacent genomic markers used in calculating the second correlating statistic, and calculating the second correlating statistic for each genomic marker according to the following equation:

$$AVGCHI(j) = \frac{\sum_{k=-NEIGHBORNU M}^{NEIGHBORNU M} WEIGHTS[k + NEIGHBORNU M] * MAX[j+k]}{\sum_{k=0}^{2*NEIGHBORNU M} WEIGHTS[k]},$$

wherein NEIGHBORNUM is the neighbor parameter, WEIGHTS is an array of weight parameters having length NEIGHBORNUM, and MAX is the first correlating statistic.

14. A computer-readable storage medium encoded with instructions that when executed on one or more processors within a computer system, perform a method for mapping one or more genomic markers to a phenotypical trait, the method comprising:

receiving a structured data set having a plurality of genomic markers;
  determining a first correlating statistic for each genomic marker where the magnitude of the correlating statistic is proportional to the capability of the genomic marker to map a phenotype;
  calculating a second correlating statistic for each genomic marker from a smoothing mathematical function of the determined first correlating statistic of the genomic marker and the first correlating statistic of adjacent genomic markers; wherein calculating includes:
    providing a neighbor parameter indicating how many adjacent genomic markers to use in calculating the second correlating statistic,
    providing a weight parameter indicating a weight to apply to each of the adjacent genomic markers used in calculating the second correlating statistic, and calculating the second correlating statistic for each genomic marker according to the following equation:

$$AVGCHI(j) = \frac{\sum_{k=-NEIGHBORNUM}^{NEIGHBORNUM} WEIGHTS[k + NEIGHBORNUM] * MAX[j+k]}{\sum_{k=0}^{2*NEIGHBORNUM} WEIGHTS[k]},$$

wherein NEIGHBORNUM is the neighbor parameter, WEIGHTS is an array of weight parameters having length NEIGHBORNUM, and MAX is the first correlating statistic.

15. The method of claim 14, further comprising:

selecting a genomic marker that satisfies a predetermined criterion; and
  using the selected genomic marker to create a decision node by splitting the structured data set into two subsets, wherein the decision node is on a binary decision tree that maps genomic markers to phenotypical trait.

16. The method of claim 15, wherein the predetermined criterion includes selecting the genomic marker with the largest second correlating statistic.

17. The method of claim 1, further comprising:

selecting a genomic marker that satisfies a predetermined criterion; and
  using the selected genomic marker to create a decision node by splitting the structured data set into two subsets, wherein the decision node is on a binary decision tree that maps genomic markers to phenotypical trait.

18. The method of claim 17, wherein the predetermined criterion includes selecting the genomic marker with the largest second correlating statistic.

19. The system of claim 13, further comprising software instructions executable on the one or more processors to cause the one or more processors to perform operations including:

selecting a genomic marker that satisfies a predetermined criterion; and
  using the selected genomic marker to create a decision node by splitting the structured data set into two subsets, wherein the decision node is on a binary decision tree that maps genomic markers to phenotypical trait.

20. The system of claim 19, wherein the predetermined criterion includes selecting the genomic marker with the largest second correlating statistic.

* * * * *